United States Patent
Schnell et al.

(10) Patent No.: US 9,901,693 B2
(45) Date of Patent: Feb. 27, 2018

(54) PRESSURE EQUALIZING DEVICE

(71) Applicant: TRACOE medical GmbH, Nieder-Olm (DE)

(72) Inventors: Ralf Schnell, Seligenstadt (DE); Andreas Hahn, Mainz-Hechtsheim (DE)

(73) Assignee: TRACOE Medical GmbH, Nieder-Olm (DE)

( * ) Notice: Subject to any disclaimer, the term of this patent is extended or adjusted under 35 U.S.C. 154(b) by 438 days.

(21) Appl. No.: 14/646,081

(22) PCT Filed: Dec. 5, 2013

(86) PCT No.: PCT/EP2013/075659
§ 371 (c)(1),
(2) Date: May 20, 2015

(87) PCT Pub. No.: WO2014/090680
PCT Pub. Date: Jun. 19, 2014

(65) Prior Publication Data
US 2015/0283343 A1 Oct. 8, 2015

(30) Foreign Application Priority Data
Dec. 11, 2012 (DE) .......... 10 2012 112 097

(51) Int. Cl.
*A61M 16/00* (2006.01)
*A61M 16/04* (2006.01)
*A61M 25/10* (2013.01)

(52) U.S. Cl.
CPC .... *A61M 16/044* (2013.01); *A61M 25/10184* (2013.11); *A61M 2205/0216* (2013.01); *A61M 2207/00* (2013.01)

(58) Field of Classification Search
CPC ............ A61M 16/0434; A61M 16/044; A61M 16/0456; A61M 25/1009; A61M 25/1018;
(Continued)

(56) References Cited

U.S. PATENT DOCUMENTS 3,468,308 A * 9/1969 Bierman ............... A61M 5/152
128/DIG. 12
3,642,005 A 2/1972 Mcginnis
(Continued)

FOREIGN PATENT DOCUMENTS

DE  100 39 045 C1  9/2001
EP  1 252 909 A2  10/2002
(Continued)

OTHER PUBLICATIONS

Agnes Wittmann-Regis, International Preliminary Report on Patentability, World Intellectual Property Organization, PCT/EP2013/075659, dated Jun. 16, 2015.

*Primary Examiner* — Joshua Lee
(74) *Attorney, Agent, or Firm* — Paul & Paul

(57) ABSTRACT

The present invention relates to a pressure equalizing device with a pressure equalizing balloon, the volume of which is connected to a further volume, the pressure of which is intended to be kept at as constant a value as possible even in the event of an enforced change in volume. In order therefore to keep the cuff pressure within the pressure range that is generally considered to be useful and optimal of between approximately 20 mbar and 30 mbar, but also make possible, if required, to increase the pressure in a controlled manner, according to the invention the equalizing balloon keeping the pressure generally constant is accommodated in a protective sleeve which has radial bulges deviating from a uniformly concave form matched to the outer contour of the balloon, which bulges are designed such that the equalizing balloon first abuts against the wall areas of the protective (Continued)

Figure 1:
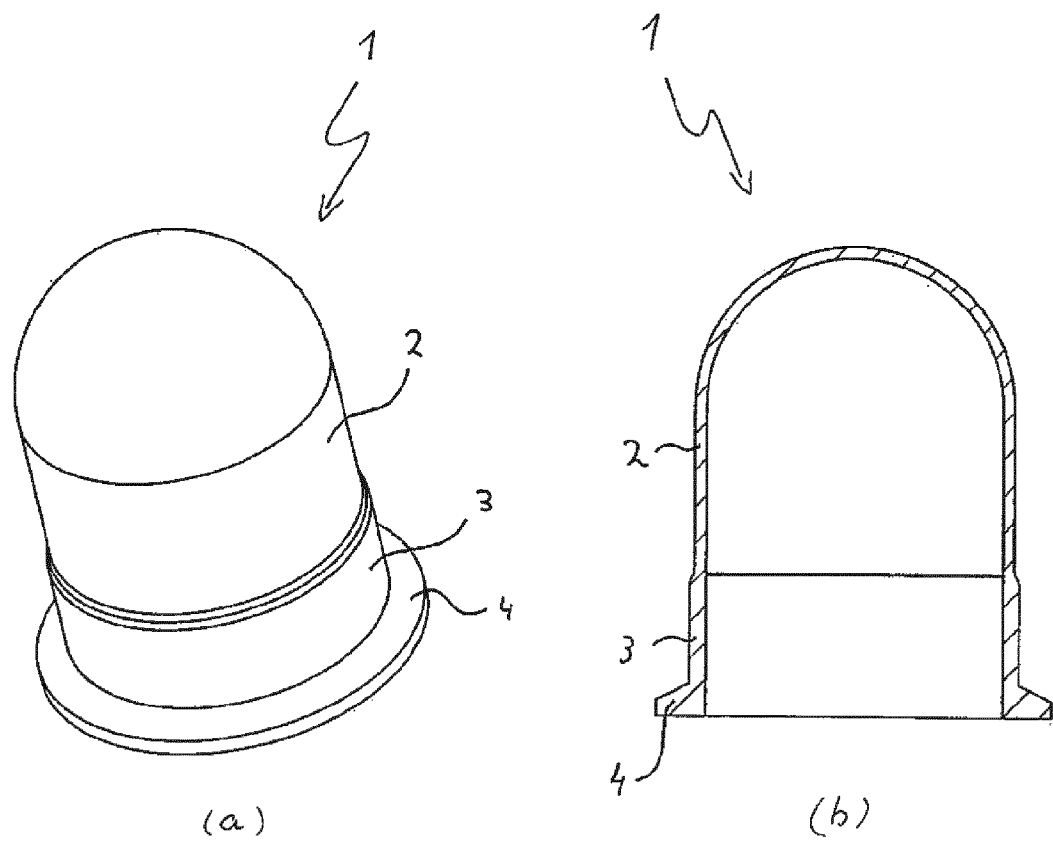

sleeve matched to the contour of the balloon and then, when pressure is increased, extends only into the bulges, whereby the pressure in the equalizing balloon gradually increases as the volume in the bulges increases.

16 Claims, 5 Drawing Sheets

(58) Field of Classification Search
CPC ...... A61M 25/10184; A61M 25/10185; A61M 25/10187; A61M 2025/1084; A61M 2205/3341; A61M 2205/3344
See application file for complete search history.

(56) References Cited

U.S. PATENT DOCUMENTS

| | | | |
|---|---|---|---|
| 3,848,605 A | 11/1974 | Harautuneian et al. | |
| 3,898,987 A * | 8/1975 | Elam | A61B 5/0875 116/70 |
| 3,980,082 A * | 9/1976 | Miller | A61B 5/0215 600/487 |
| 4,119,101 A | 10/1978 | Igich | |
| 4,227,534 A * | 10/1980 | La Rosa | A61M 25/1018 604/214 |
| 4,245,639 A * | 1/1981 | La Rosa | A61M 25/0017 604/214 |
| 4,501,273 A | 2/1985 | Mcginnis | |
| 4,648,406 A * | 3/1987 | Miller | A61B 5/03 600/487 |
| 4,856,510 A | 4/1989 | Kowalewski | |
| 5,038,777 A * | 8/1991 | Dunn | A61M 16/04 128/207.14 |
| 5,462,528 A * | 10/1995 | Roewer | A61M 25/1009 128/207.14 |
| 2008/0078403 A1* | 4/2008 | Clayton | A61L 29/04 128/207.15 |
| 2012/0017897 A1* | 1/2012 | Ranganathan | A61M 16/04 128/202.22 |
| 2012/0090619 A1 | 4/2012 | Levine | |

FOREIGN PATENT DOCUMENTS

| | | |
|---|---|---|
| GB | 1 423 789 A | 2/1976 |
| WO | 9110465 A1 | 7/1991 |

* cited by examiner

PRESSURE EQUALIZING DEVICE

CROSS-REFERENCE TO RELATED APPLICATION

This is a national stage 371 application of International Application No. PCT/EP2013/075659, filed Dec. 5, 2013.

The present invention concerns a pressure equalization device comprising a pressure equalization balloon, wherein the volume of the pressure equalization balloon is connected to a further volume, the pressure of which is to maintain a substantially constant value even in the event of a forced change in volume at least within a predetermined volume range of the pressure equalization balloon.

Such a volume, the pressure of which is to maintain a value which is as constant as possible even in the event of a change in volume imposed from the exterior, is for example the volume of the inflation cuff of a respiration cannula. The inflation cuff which in medical technical language and hereinafter is also referred just as the "cuff" in that case surrounds a cannula introduced into the trachea (windpipe) of a patient and after insertion of the cannula is inflated to a low pressure of the order of magnitude of between 20 and 30 mbars so that it bears sealingly against the wall of the trachea, in that way fixes the cannula and also prevents secretions which collect above the cuff in the area around the respiration cannula passing into the bronchial tubes or the lungs of the patient. Otherwise such secretions in which germs very quickly multiply and which then pass into the deeper airways or the lungs lead to severe complications like for example lung inflammation.

A good sealing effect by such a cuff is of great significance in particular in the case of patients undergoing long-term ventilation. The cannula in that case can either be an endotracheal tube which is introduced through the mouth and pharynx of the patient but it can also equally well be a tracheostomy cannula which is passed through a surgically produced opening (a tracheostoma) in the neck of a patient and thus connects the trachea to the ambient air or a ventilation device, by-passing the oral and pharyngeal cavity.

Particularly in the case of patients undergoing long-term ventilation in that case the set cuff pressure is also of very great significance as that pressure may not permanently exceed a pressure of 30 mbars because the pressure acting on the highly sensitive wall of the trachea can lead to impairment of blood circulation and as a result injury or wounds going as far as necrosis effects.

On the other hand the cuff pressure may also not be too low in order to prevent the above-mentioned secretion from passing the cuff. In addition air flowing uncontrolledly past the cuff could also trigger a false alarm on a ventilation device as ventilation when using corresponding cannulas is basically to be effected by way of the lumen of the cannula and is controlled on the basis of the flow of air through the cannula.

In order therefore to keep the cuff pressure in the pressure range which is generally deemed to be appropriate and optimum of between about 20 mbars and 30 mbars numerous devices have already been used and described which are intended to keep the pressure in the cuff constant. In that respect it is to be borne in mind that the trachea cross-section can also change due to a patient moving, turning or inclining the head and thus presses on the cuff in different ways and changes the volume thereof. The cuff therefore has to be connected to a suitable pressure reservoir by way of a suitable hose which is generally guided along the cannula or integrated into the wall of the cannula, which pressure reservoir can receive air or generally filling gas like for example nitrogen from the cuff depending on the respective change in volume of the cuff and also return it to the cuff again in order to keep the cuff pressure at a constant value independently of a variation in the volume of the cuff which possibly occurs.

For example electronic pressure regulators are known for that purpose, like also simple compensating volumes, in particular balloons, wherein generally the pressure of a cuff is checked and adjusted by qualified medical staff at certain time intervals, but often only once in a shift.

In addition a system is also already known, which operates with a latex balloon as a compensating volume, wherein the latex balloon has the property of maintaining a constant pressure at least within a certain range of volume. In other words, a slight increase in the pressure already leads to a corresponding increase in volume of the latex balloon while a slight reduction in pressure again leads to a reduction in volume of the latex balloon so that as a result the pressure in a cuff connected to a corresponding latex balloon remains at the same approximately constant value. To protect the very thin and delicate latex balloon which has the desired properties, it is arranged in an external protective sheath or case which is preferably transparent, which is substantially spherical and which is sufficiently stable to protect the balloon accommodated in the case in relation to shocks, damage or pressure exerted from the exterior, and it will be appreciated that the protective case must be air-permeable in order not to influence expansion or contraction of the equalization balloon within the protective case.

Various apparatuses for keeping constant or monitoring the pressure of corresponding cuffs or cuff devices in the medical area are known from U.S. Pat. Nos. 3,642,005 and 4,501,273, US patent application No 2012/0090619 A1, EP 1 252 909 A2 and British patent GB 1 423 789.

Electronic pressure regulating systems are very complicated and expensive. Balloon systems with very voluminous equalization balloons are cumbersome to handle and involve the risk of damage to such a balloon. The known system with an equalization balloon of latex, which is disposed within a stable transparent protective case, in principle operates relatively well but suffers from the disadvantage that the latex inter alia by virtue of its allergenic potential is undesirable or indeed unacceptable in many areas of medical treatment.

EP 1 252 909 A2 already describes a system comprising a main balloon (corresponding to the cuff) and a pilot balloon, wherein the main balloon and the pilot balloon are to involve the same elasticity so that the condition or also in particular the pressure of the main balloon (cuff) can be read off on the basis of the condition of the visible pilot balloon. In that respect EP 1 252 909 describes a material of thermoplastic elastomers on a styrene base both for the main balloon and also for the pilot balloon.

Even if the pressure in the cuff of a respiration cannula is generally to be kept constant, there are situations in every day medical occurrences in which such a cuff is to be acted upon with a higher pressure deliberately and generally only for a short time, which higher pressure for example is between 30 and 50 mbars. That can scarcely be implemented with the above-mentioned pressure equalization balloons which always further expand with an only slightly increasing pressure. It is admittedly known for such a balloon to be provided with a fixed protective case which prevents further stretching beyond the volume of the protective case. This however means that the pressure suddenly rises very greatly as soon as the equalization balloon has come to bear against the inside wall of the protective case. A well-controlled increase to an only slightly increased pressure of for example between about 30 and 50 mbars is in that case scarcely possible.

In comparison with that state of the art the object of the present invention is to provide a pressure compensation equalization device which on the one hand keeps substantially constant a predetermined pressure in another volume connected to the equalization balloon like for example a cuff or a cuff device, but which also makes it possible to increase the pressure in controlled fashion as required.

That object is attained in that the equalization balloon which keeps the pressure generally constant is accommodated in a protective case which has radial outward bulges deviating from a uniformly concave shape matched to the outside contour of the balloon, which bulges of such a configuration that the equalization balloon firstly bears against the wall regions of the protective case, that are matched to the contour of the balloon, and then upon an increase in pressure expands only into the outward bulges, whereby the pressure in the equalization balloon gradually increases with the increase in volume into the outward bulges.

It is desirable in that case if in the volume range of the equalization balloon between the volume upon bearing against the regions matched to the contour of the free balloon and the volume upon complete filling of all outward bulges, it gradually rises and preferably approximately by the factor of two.

The difference in volume between the volume upon bearing against the regions matched to the contour of the free balloon and the volume upon complete filling of all outward bulges should approximately be at least 5% of the first-mentioned volume. The relative surface area proportion of the concave bulges 6 relative to the convex portions 5$a$ can be for example between 20% and 70%.

In a preferred embodiment the equalization balloon is produced from a thermoplastic polymer and prior to the first use was overstretched beyond the maximum intended regulating volume and was then relaxed to the range of the regulating volume, as is described in the patent application filed at the same time to the same applicant and bearing the title "pressure equalization balloon and method for the production thereof".

Desirably a suitable equalization balloon is produced for use on respiration cannulas, with an initial volume (prior to the overstretching effect) of between about 3 and 8 cm$^3$, which has increased after the first-time overstretching for example to a volume of between about 200 cm$^3$ (or even more), by between about 20 and 50%. The regulating volume could then be in the range of for example between 10 or 20 and 100 cm$^3$, preferably in the range of between 30 and 70 cm$^3$.

The present invention however is not limited to such a balloon of thermoplastic polymers but can be applied to all kinds of balloons which have a suitable pressure characteristic, which firstly exhibits no or almost no increase in pressure with increasing volume, but the pressure of which is to markedly increase as from a given volume.

The equalization balloon is enclosed by a protective case which protects the relatively delicate equalization balloon from external mechanical effects. Such a protective case, for example of stable transparent plastic material, is of a spherical basic shape with outward bulges or outwardly shaped portions. The protective case can be for example of a diameter of the order of magnitude of between 50 and 60 mm.

As already mentioned a corresponding spherical protective case of Plexiglas or any other suitable stable plastic material can be of a diameter of the order of magnitude of between 50 and 60 mm and thus of a volume of the order of magnitude of between 70 and 100 cm$^3$. The protective case can possibly also be kept smaller and can be of a diameter of 40 mm and down to 30 mm or less. It will be appreciated that the corresponding protective case has at least one opening which connects the interior of the protective case to the environment in order to always maintain the constant ambient pressure outside the equalization balloon so that the equalization balloon can expand and contract unimpededly within the volume of the protective case.

It is however provided in that respect that the protective case, starting from its spherical basic shape, has some outward bulges which are preferably arranged strip-like. That for example provides that the equalization balloon initially expands upon a slight increase in pressure until it bears against parts of the inside wall of the protective case while thereafter further expansion of the equalization balloon is possible only in the region of the outward bulges. That provides a slight but markedly perceptible and visible increase in pressure until the outward bulges are also filled with the balloon, whereupon the pressure rises steeply upon a further feed of gas. In the transitional range in which the balloon expands into the outward bulges however a comparatively slight continuous rise in pressure is to be noted, which makes it possible to set in targeted and controlled fashion a higher cuff pressure which is desired at times. That is required for example in some emergency situations if for example bleeding occurs in the trachea or in the neck and pharynx cavity and has to be stopped without the sealing contact of the cuff against the trachea wall being abandoned but even has to be possibly increased.

A particular advantage of the use of thermoplastic polymers is that a corresponding balloon can be produced using an injection molding process, which permits a very well controllable, uniform wall thickness, in which respect the wall thickness in turn is one of the parameters by which the specific regulating pressure can be set. A second parameter for setting a regulating pressure involves the extent of the overstretching effect.

Styrene-based thermoplastic polymers have proven to be particularly suitable like for example SBS (styrene-butadiene-styrene), SIS (styrene-isoprene-styrene) and SEPS (styrene-ethylene-propylene-styrene). The material SEBS (styrene-ethylene-butylene-styrene) is particularly preferred for the present invention.

The thermoplastic material may also have fillers like for example mineral oils and in particular medical white mineral oils.

Desirably the thermoplastic material is so selected or set that it has a Shore 00 hardness (in accordance with ISO 868) of 30-70, preferably 50 Shore 00. The tensile modulus at 100% stretching is typically in the range of between 40-150 kPa (in accordance with ISO 37).

The wall thickness of the pressure-less balloon prior to the first-off overstretching, that is to say after the injection molding process, can be for example in the range of between 0.4 and 1.5 mm. Upon stretching of such a balloon and in particular for overstretching thereof a pressure of the order of magnitude of between 40 and 60 mbars is typically required. If however the balloon is allowed to relax again after adequate overstretching and to go back into the pressure-less condition then in that condition it is on the one hand of a generally somewhat larger volume than after the injection molding operation, but in particular it has a different stretching characteristic, that is to say the pressure which is required to inflate the balloon within the regulating volume range (typically less than a quarter of the overstretching volume) is however only still at about half the pressure which is required for the first-time stretching and overstretching of the balloon and it remains substantially constant over a greater volume range of the balloon. As stated the precise value can be relatively accurately set by specifically targeted choice of the wall thickness and by the controlled extent of the overstretching.

Admittedly the material occasionally has a certain "recovery effect" if it was kept in the pressure-less condition for a prolonged period of time, which has the result that, when being inflated again for the first time, the regulating pressure value has to be somewhat exceeded; if however the available regulating volume (which for example is delimited by the protective case) is once again completely put to use before the balloon is brought into operation then the desired stretch characteristic at the regulating pressure is very quickly restored again.

A further advantage of production by means of injection molding processes is that the equalization balloon can be produced selectively with different wall thicknesses at various locations. In particular a preferred embodiment of the invention provides that the equalization balloon has a reinforced opening ring which surrounds the balloon opening and whose wall thickness is at least 50% greater than the wall thickness of the balloon elsewhere and which accordingly does not take part in the stretching effect upon pressure equalization. Such an opening ring can be produced with an accurately defined geometry and wall thickness so that for example it can be fitted directly on to a suitable standard connection (for example a Luer connector) in sealing engagement therewith.

The opening ring can in particular also have a peripherally extending sealing flange which can be easily fixed to a suitable connecting portion of the connecting line to a cuff.

Corresponding standard connections are typically of a diameter in the range of between 12 and 25 mm.

The balloon should desirably be produced in such a way that the usable regulating volume includes the range of between 10 and 100 cm$^3$, desirably the range of between 20 and 80 cm$^3$. The maximum regulating volume is desirably delimited by a stable transparent outer protective case. In that way the balloon is visible in the interior of the transparent case and the technical staff who operate the corresponding ventilation apparatuses can directly see, on the basis of the condition of the balloon, whether the pressure in the cuff is in the desired range.

Figure 2:
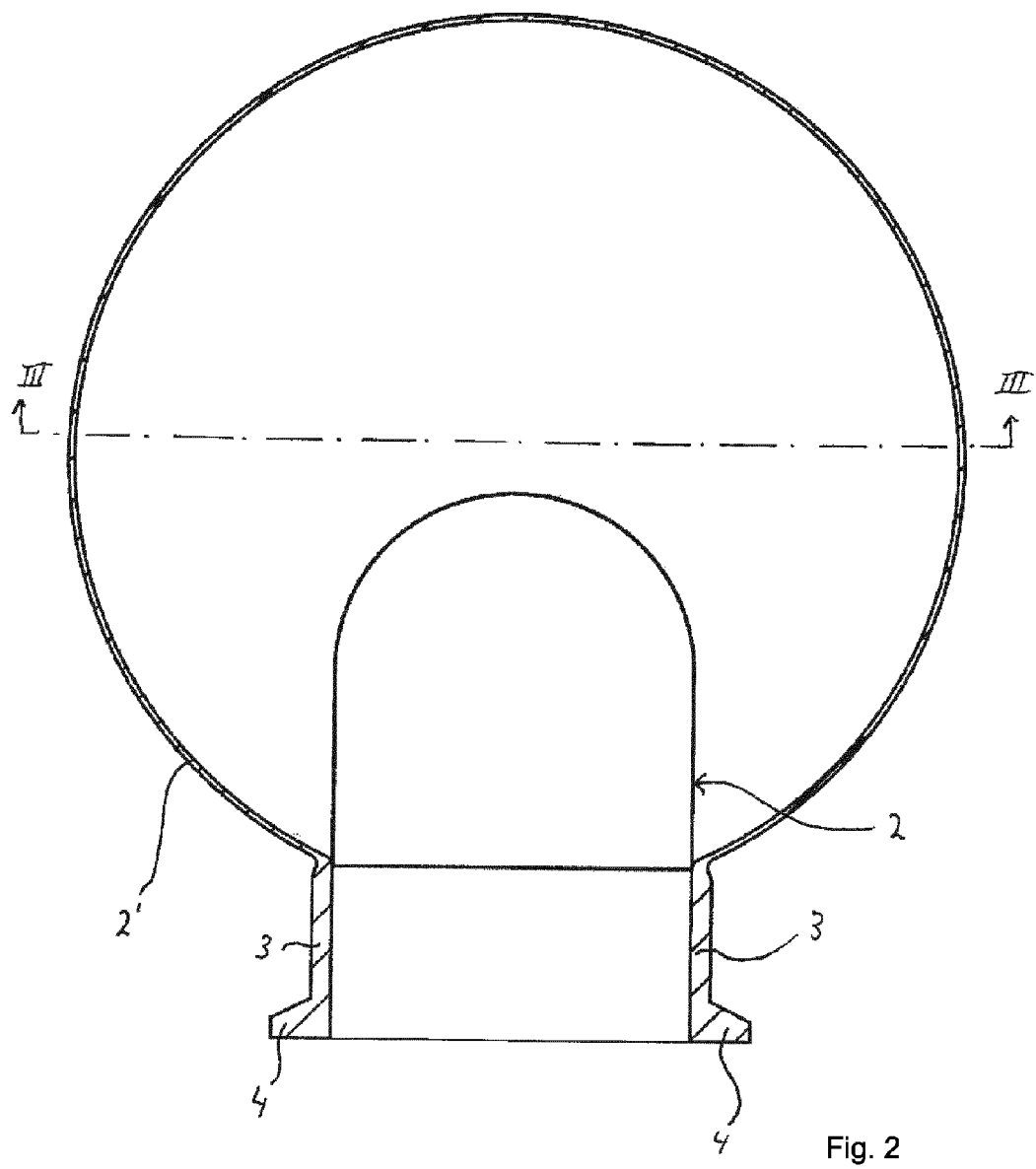
Figure 3:
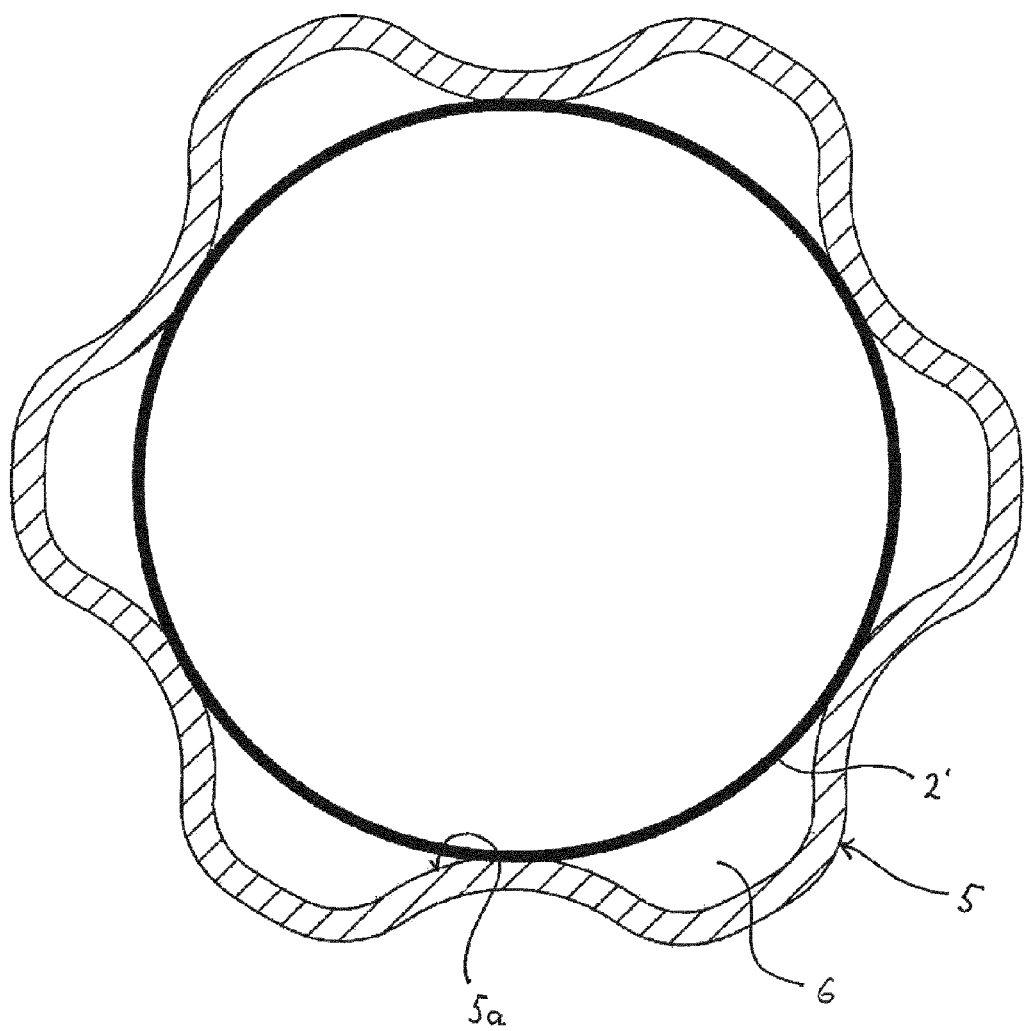
Figure 5:
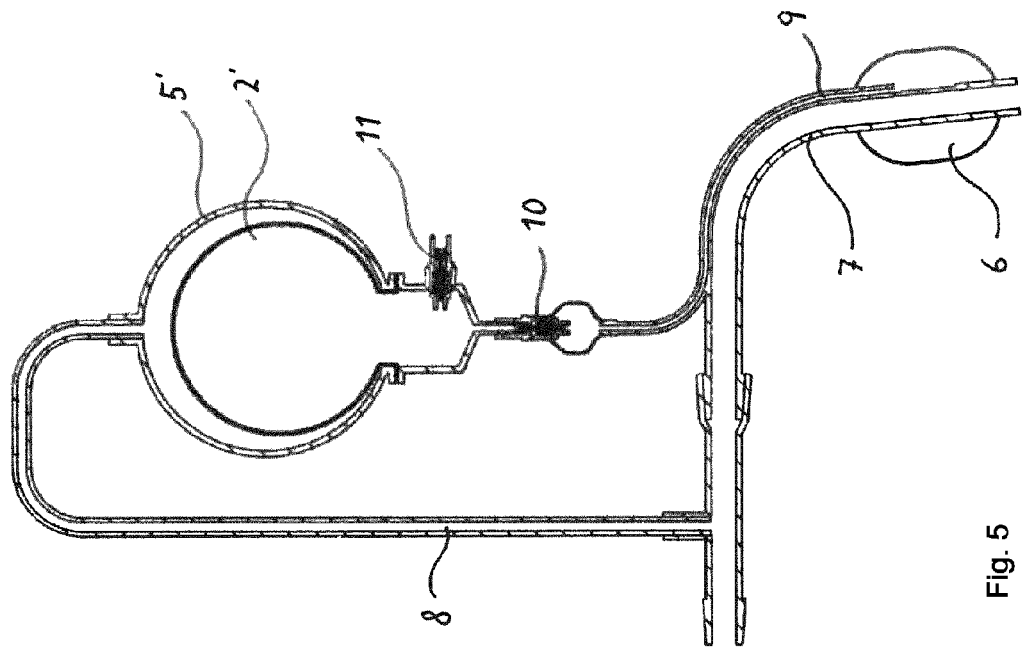
Figure 4:
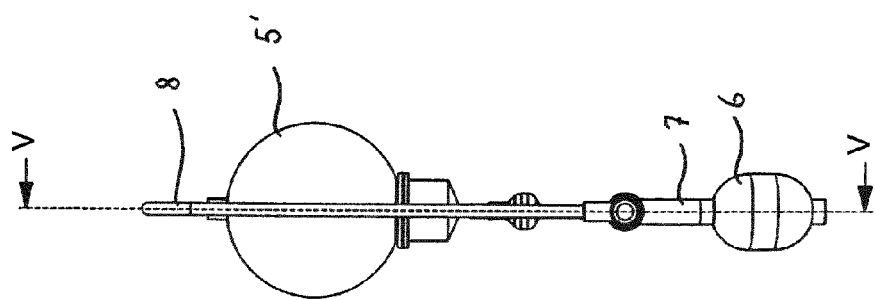
Figure 6:
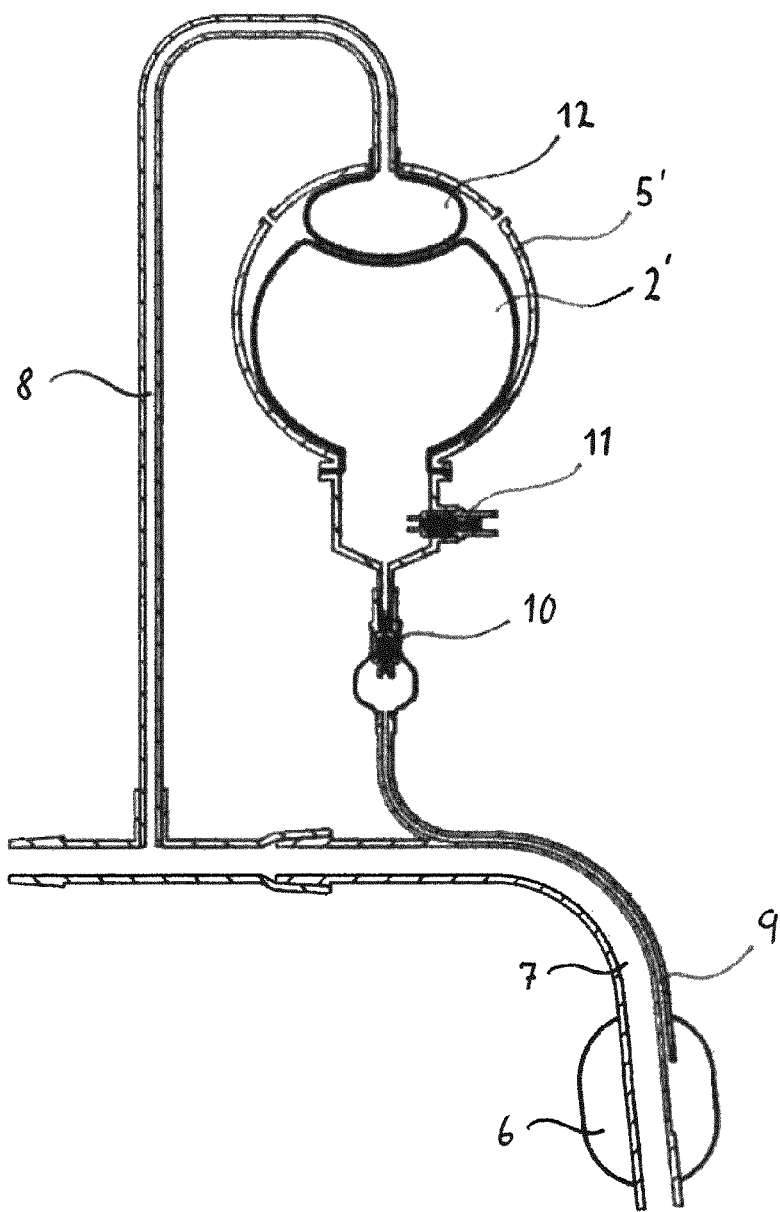

Further advantages, features and possible uses of the present invention will be apparent from the following description of a preferred embodiment and the accompanying Figures in which:

FIG. 1 shows a perspective view in the left-hand part and a vertical sectional view in the right-hand part through an equalization balloon according to the invention in the pressure-less condition as is the case for example immediately after production using an injection molding process, FIG. 2 shows a pressure equalization balloon in the inflated condition as occurs during pressure regulation, wherein the contour of the pressure-less balloon is also indicated, FIG. 3 shows a cross-section through the balloon of FIG. 2 corresponding to line III-III with a protective case additionally arranged around the balloon, FIG. 4 shows a diagrammatic view of a further embodiment of the present invention, FIG. 5 shows a sectional view of the FIG. 4 embodiment corresponding to the section line V-V in FIG. 4, and FIG. 6 shows a sectional view similar to FIG. 5 of a still further modified embodiment.

FIG. 1 shows a pressure equalization balloon 1 comprising a dome-shaped stretch portion 2, a cylindrical portion 3 of a somewhat greater wall thickness and finally a flange portion 4, the portions 3 and 4 forming an opening and connecting portion of the pressure equalization balloon 1. For example the portions 3 and 4 can be fitted on to a Luer connector which is typical in the medical area, that is to say a pipe connection portion of a suitable diameter, wherein the free inside diameter of the portions 3 and 4 is preferably somewhat smaller than the outside diameter of the tube connection portion on to which that connecting portion is fitted so that it bears under a slight elastic stress sealingly against the outside of the pipe connection portion. A clamping ring or clamping band can also be arranged around the portion 3, which securely holds the balloon fast to the pipe connection portion, with the flange portion 4 serving as a securing arrangement.

FIG. 2 shows the stretch portion 2 in a stretched condition, the stretch portion being identified in the stretched condition by reference to 2'. The contour of the unstretched portion 2 is also shown at the same time. The size relationships between the stretch portion 2' in the stretched condition and in the pressure-less condition 2 approximately realistically reproduce the size relationship in a typical regulating range in which the pressure in the interior of the equalization balloon 2 remains substantially constant independently of the volume. In other words, a very slight increase in the pressure leads directly to a corresponding stretching of the portion 2', which stretching reduces the pressure to the regulating value again. Conversely, a slight drop in pressure already leads to a reduction in the volume of the portion 2' so that the regulating pressure is then also restored.

FIG. 3 shows a particular embodiment of the present invention with a protective sleeve or case 5 comprising a material which is relatively strong and practically non-stretchable in comparison with the pressure equalization balloon 1 and which is preferably transparent so that it is possible to see the actual condition of the pressure equalization balloon 1 through the protective case 5.

In general the protective case 5 could be spherical with an opening portion corresponding to the connecting portion 3, 4 of the pressure equalization balloon 1 so that the stretch portion 2', upon reaching a radius corresponding to the inside radius of the protective case, would bear over the full surface area against the inside wall of the protective case so that, in the case of a further feed of gas into the interior of the balloon, the pressure would rise immediately and substantially proportionally to the increase in the amount of gas.

The protective case 5 in FIG. 3 however deviates from a spherical shape by virtue of the fact that it has strip-shaped outward bulges 6 which start from the lower opening region, as can be very clearly seen in the sectional view in FIG. 3, whereas the section perpendicularly to the plane of FIG. 3 would still substantially reproduce a spherical shape or from the inside a purely concave shape for the protective case 5. The result of that design configuration is that the stretch portion 2', after reaching a radius corresponding to the radius of the convex portions of the protective case 5, bears against the inside wall 5a of those convex portions, which in that region no longer allow further stretching of the portion 2'. Upon a further feed of gas or upon an increase in the pressure therefore the stretch portion has to stretch out into the bulges 6. That limitation on the stretching of the portion 2' along the walls 5a of the convex regions of the protective case leads to a modified stretch/pressure characteristic in respect of the pressure equalization balloon 1 so that, after the balloon has reached a volume at which the stretch portion bears against the wall portions 5a, the pressure upon a further feed of gas no longer remains constant but rises slightly linearly. In that way it is possible for the pressure to be increased in a relatively controlled fashion from the normal regulating pressure, gradually and continuously, to a pressure as occurs after the bulges 6 are filled out by the parts of the stretch portion 2', which expand thereinto. That permits markedly easier adjustment of a given pressure value between the regulating pressure and the above-mentioned final pressure which can be for example approximately twice the regulating pressure. If therefore the regulating pressure is in the range of between 20 and 25 mbars the final pressure could be between 40 and 50 mbars, in which case that final pressure can be varied within relatively large ranges by a suitable configuration for the bulges 6 and the convex portions therebetween.

A correspondingly higher pressure in the cuff of a respiration cannula is required for example to stop bleeding or if certain treatments or technical measures are to be conducted on the patient or a respiration cannula, which are inevitably linked to greater movements of the cannula, in which case however the sealing integrity of the cuff in the trachea is not to be impaired.

FIG. 4 diagrammatically shows a complete respiration system comprising a respiration cannula 7 with a cuff 6 and a pressure equalization balloon accommodated in a spherical protective case 5'. The details of this embodiment can be even better seen in the sectional view in FIG. 5. FIG. 5 diagrammatically shows the respiration cannula 7, the cuff 6 surrounding the cannula 7 and serving to seal off the intermediate space between the wall of the trachea and the outside of the cannula 7, with a filling hose 9 connecting the interior of the cuff 6 to a pressure equalization balloon 2', wherein in this case there is additionally also provided a damping valve 10 in the filling hose 9 or the connection thereof to the pressure equalization balloon 2', which serves to damp the possible flow of air or gas out of the cuff 6 into the equalization balloon 2'. Upon artificial respiration and also upon spontaneous breathing the pressure in the lungs and the trachea of the patient varies, whereby in turn pressure is exerted from the exterior on the cuff 6, which pressure thereby urges air by way of the filling hose 9 into the equalization balloon 2'. In that case there is a risk that the cuff 6 no longer bears sealingly against the wall of the trachea.

Instead the air or the filling gas should remain for somewhat longer in the cuff 6, in which case a short-term increase in pressure is also tolerated, so that during a respiration pressure peak the sealing integrity of the contact between the cuff 6 and the wall of the trachea remains guaranteed. The damping valve 10 provides that the pressure in the cuff 6 can be higher than the pressure in the equalization balloon at least for a short time, that is to say during corresponding respiration pressure peaks. In the reversed direction however the damping valve 10 is transmissive so that a drop in the pressure in the cuff 6 is immediately compensated. The valve 11 serves for filling the cuff and the equalization balloon with a predetermined amount of filling gas (for example air or nitrogen).

In the respiration system according to the invention an alternative to the damping valve 10 or a supplement thereto lies in a connecting hose 8 between the cannula 7 and the protective case 5', which in this embodiment is also or can be spherical.

Respiration pressure peaks as occur both upon artificial respiration and also in spontaneous respiration and which act on the cuff 6 from the exterior occur primarily in the interior of the respiration cannula 7 so that the corresponding pressure peaks are also transmitted into the interior of the protective case 5' by way of the connecting hose 6 and thus also act on the equalization balloon 2' from the exterior. The system overall remains better in an equilibrium condition by virtue of simultaneous pressurization both of the equalization balloon 2' and also the cuff 6 from the exterior.

It will be noted however that this means that the internal pressure in the cuff additionally rises by the full pressure of a respiration air peak. If therefore the respiration pressure is 20 mbars and the cuff pressure is also 20 mbars and the respiration pressure is transmitted into the protective case 5' by way of the connecting hose 8 the pressure in the pressure equalization balloon 2' and also in the cuff 6 rises by 20 mbars so that the cuff pressure is overall already 40 mbars, which could be unwanted in the long term.

In order to somewhat damp that effect the FIG. 6 embodiment also involves a modification to the effect that it is not the overall volume of the protective case 5' that is acted upon with the respiration pressure from the cannula 7, but only a further transmission balloon 12 which is in contact only with a part of the surface of the pressure equalization balloon 2' so that the pressure in the interior of the equalization balloon 2' does not rise by the full value of the respiration pressure.

For the purposes of the original disclosure it is pointed out that all features as can be seen by a man skilled in the art from the present description, the drawings and the appended claims, even if they are described in specific terms only in connection with certain other features, can be combined both individually and also in any combinations with others of the features or groups of features disclosed herein insofar as that has not been expressly excluded or technical aspects make such combinations impossible or meaningless. A comprehensive explicit representation of all conceivable combinations of features and emphasis of the independence of the individual features from each other is dispensed with here only for the sake of brevity and readability of the description.

The invention claimed is:

1. A pressure equalization device comprising:
   a pressure equalization balloon connected to a cuff, wherein the pressure equalization balloon is configured to maintain a pressure in the cuff in the event of a forced change in volume of the cuff; and
   a rigid protective case housing the pressure equalization balloon and comprising radially outward bulges;
   wherein an increase in pressure within the pressure equalization balloon causes the pressure equalization balloon to expand into the radially outward bulges, whereby a pressure in the pressure equalization balloon gradually increases with the increase in volume into the outward bulges.

2. A pressure equalization device as set forth in claim 1 characterised in that the volume of the outward bulges of the protective case is at least 5% of the volume of the protective case without the outward bulges.

3. A pressure equalization device as set forth in claim 1 characterised in that the pressure equalization balloon comprises a styrene-based thermoplastic elastomer.

4. A pressure equalization device as set forth in claim 1 characterised in that the balloon is produced by injection molding.

5. A pressure equalization device as set forth in claim 1 characterised in that a wall thickness of the balloon is between 0.4 and 1.5 mm.

6. A pressure equalization device as set forth in claim 1 characterised in that the balloon has a reinforced opening ring which extends around a balloon opening and whose wall thickness is at least 50% greater than a wall thickness of the balloon elsewhere.

7. A pressure equalization device as set forth in claim 1 characterised in that dimensions of the opening ring are matched to a standard connection of a diameter of between 12 and 25 mm.

8. A pressure equalization device as set forth in claim 1 characterised in that a regulating volume of the balloon is between 10 and 100 cm$^3$.

9. A pressure equalization device as set forth in claim 1 characterised in that a regulating volume of the balloon is between 20 and 80 cm$^3$.

10. A pressure equalization device as set forth in claim 1 characterised in that the balloon prior to the first use is subjected to an overstretching to a volume which is at least four times a maximum regulating volume.

11. A pressure equalization device as set forth in claim 1 characterised in that the balloon is set to a regulating value (target pressure range) of between 20 and 30 mbars.

12. A pressure equalization device as set forth in claim 1 characterised in that the protective case has strip-shaped outward bulges.

13. A pressure equalization device as set forth in claim 3 characterised in that the thermoplastic elastomer is SBS (styrene-butadiene-styrene).

14. A pressure equalization device as set forth in claim 3 characterised in that the thermoplastic elastomer is SIS (styrene-isoprene-styrene).

15. A pressure equalization device as set forth in claim 3 characterised in that the thermoplastic elastomer is SEPS (styrene-ethylene-propylene-styrene).

16. A pressure equalization device as set forth in claim 3 characterised in that the thermoplastic elastomer is SEBS (styrene-ethylene-butylene-styrene).

* * * * *